United States Patent
Hall et al.

[11] Patent Number: 5,340,837
[45] Date of Patent: Aug. 23, 1994

[54] BENZOPHENONEHYDRAZONES

[75] Inventors: Roger G. Hall, Aesch; Alfons Pascual, Basel; Odd Kristiansen, Mölin, all of Switzerland

[73] Assignee: Ciba-Geigy Corporation, Ardsley, N.Y.

[21] Appl. No.: 83,245

[22] Filed: Jun. 25, 1993

[30] Foreign Application Priority Data

Jul. 7, 1992 [CH] Switzerland .................. 2147926

[51] Int. Cl.$^5$ .................................. C07D 307/87
[52] U.S. Cl. .................... 514/603; 514/605; 514/610; 514/638; 514/639; 558/54; 558/55; 558/58; 558/56; 558/57; 564/250; 564/251
[58] Field of Search ............ 514/639, 638, 603, 610, 514/605; 558/54, 58, 55; 564/250, 251

[56] References Cited

U.S. PATENT DOCUMENTS

| | | | |
|---|---|---|---|
| 4,344,893 | 8/1982 | Copping et al. | 558/55 |
| 4,895,871 | 1/1990 | Lutomski et al. | 514/469 |

FOREIGN PATENT DOCUMENTS

| | | |
|---|---|---|
| 0003913 | 9/1979 | European Pat. Off. |
| 0026040 | 4/1981 | European Pat. Off. |
| 0355832 | 2/1990 | European Pat. Off. |
| 0500111 | 8/1992 | European Pat. Off. |

OTHER PUBLICATIONS

Acta Chemica Sandenavica, "The Synthesis of N-alkylidone-N"-sulfonylformamidrazones," B 34, 223-224 (1980).
Organic Magentic Resonance, vol. 14, 1980, p. 135-137.
Derwent 91-136915/19, 1989.
Chem. Abst. 116:209731x (1992).

*Primary Examiner*—Jose' G. Dees
*Assistant Examiner*—Dwayne C. Jones
*Attorney, Agent, or Firm*—Marla J. Mathias

[57] ABSTRACT

Compounds of the formula

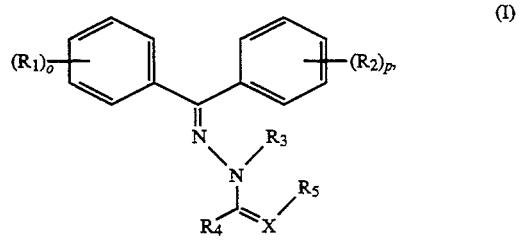

(I)

wherein
  each of o and p, independently of the other, is 0, 1, 2, 3, 4 or 5, the radicals $R_1$ being the same or different when o is greater than 1 and the radicals $R_2$ being the same or different when p is greater than 1;
  each of $R_1$ and $R_2$, independently of the other, is $C_1$-$C_4$alkyl, halo-$C_1$-$C_4$alkyl, halogen, $-NO_2$, $-OH$, $C_1$-$C_4$alkoxy, halo-$C_1$-$C_4$alkoxy, $C_1$-$C_4$alkylthio, halo-$C_1$-$C_4$alkylthio, $-O-S(=O)-R_6$, $-O-S(=O)_2-R_6$, phenoxy or $-N(R_{11})SO_2R_{12}$ and/or two substituents $R_1$ and/or two substituents $R_2$ are, independently of one another, together $-Y-Z-Y-$;
  $R_3$ is hydrogen, $C_1$-$C_4$alkyl or halo-$C_1$-$C_4$alkyl;
  $R_4$ is hydrogen, $C_1$-$C_4$alkyl, halo-$C_1$-$C_4$alkyl, unsubstituted phenyl or naphthyl or mono- or di-substituted phenyl or naphthyl;
  $R_5$ is $-S-R_7$, $-S(=O)-R_7$, $-S(=O)_2-R_7$, $-NO_2$, $-CN$, $-C(=O)-R_8$ or $-C(=O)-OR_8$;
  $R_6$ is $C_1$-$C_8$alkyl, or halo-$C_1$-$C_8$alkyl or phenyl;
  X is N or C($R_9$);
  each Y, independently of the other, is O or S; and
  Z is methylene, eth-1,2-ylene, halomethylene or haloeth-1,2-ylene;
  and the tautomers and salts thereof can be used as pesticidal compositions and can be prepared in a manner known per se.

19 Claims, No Drawings

BENZOPHENONEHYDRAZONES

The invention relates to compounds of the formula

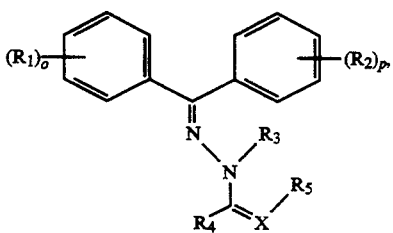

wherein
- each of o and p, independently of the other, is 0, 1, 2, 3, 4 or 5, the radicals $R_1$ being the same or different when o is greater than 1 and the radicals $R_2$ being the same or different when p is greater than 1;
- each of $R_1$ and $R_2$, independently of the other, is $C_1$–$C_4$alkyl, halo-$C_1$–$C_4$alkyl, halogen, —$NO_2$, —OH, $C_1$–$C_4$alkoxy, halo-$C_1$–$C_4$alkoxy, $C_1$–$C_4$alkylthio, halo-$C_1$–$C_4$alkylthio, —O—S(=O)—$R_6$, —O—S(=O)$_2$—$R_6$, phenoxy or —N($R_{11}$)$SO_2R_{12}$ and/or two substituents $R_1$ bonded to vicinal carbon atoms of the phenyl ring and/or two substituents $R_2$ bonded to vicinal carbon atoms of the phenyl ring are, independently of one another, together —Y—Z—Y—;
- $R_3$ is hydrogen, $C_1$–$C_4$alkyl or halo-$C_1$–$C_4$alkyl;
- $R_4$ is hydrogen, $C_1$–$C_4$alkyl, halo-$C_1$–$C_4$alkyl, unsubstituted phenyl or naphthyl or mono-or di-substituted phenyl or naphthyl, the substituents being selected from the group consisting of halogen, $C_1$–$C_4$alkyl, halo-$C_1$–$C_4$alkyl, $C_1$–$C_4$alkoxy, halo-$C_1$–$C_4$alkoxy, $C_1$–$C_4$alkylthio, halo-$C_1$–$C_4$alkylthio, —$NO_2$ and —CN;
- $R_5$ is —S—$R_7$, —S(=O)—$R_7$, —S(=O)$_2$—$R_7$, —$NO_2$, —CN, —C(=O)—$R_8$ or —C(=O)—$OR_8$;
- $R_6$ is $C_1$–$C_8$alkyl, or halo-$C_1$–$C_8$alkyl or phenyl;
- $R_7$ is $C_1$–$C_8$alkyl, $C_3$–$C_6$cycloalkyl, halo-$C_1$–$C_8$alkyl, unsubstituted or mono- or di-substituted phenyl, the substituents being selected from the group consisting of halogen, $C_1$–$C_4$alkyl, halo-$C_1$–$C_4$alkyl, $C_1'$–$C_4$alkoxy, halo-$C_1$–$C_4$alkoxy, $C_1$–$C_4$alkylthio, halo-$C_1$–$C_4$alkylthio, —$NO_2$ and —CN; benzyl or unsubstituted or mono- or di-substituted amino, the substituents being selected from the group consisting of $C_1$–$C_4$alkyl, halo-$C_1$–$C_4$alkyl and phenyl;
- $R_8$ is $C_1$–$C_8$alkyl, halo-$C_1$–$C_4$alkyl or unsubstituted or mono- or di-substituted phenyl, the substituents being selected from the group consisting of halogen, $C_1$–$C_4$alkyl, halo-$C_1$–$C_4$alkyl, $C_1$–$C_4$alkoxy, halo-$C_1$–$C_4$alkoxy, $C_1$–$C_4$alkylthio, halo-$C_1$–$C_4$alkylthio, —$NO_2$ and —CN;
- X is N or C($R_9$);
- each Y, independently of the other, is O or S;
- Z is methylene, eth-1,2-ylene, halomethylene or haloeth-1,2-ylene;
- $R_9$ is hydrogen, $C_1$–$C_4$alkyl, halo-$C_1$–$C_4$alkyl, —CN, —C(=O)—$R_{10}$ or —C(=O)—$OR_{10}$;
- $R_{10}$ is hydrogen, $C_1$–$C_8$alkyl or halo-$C_1$–$C_8$alkyl;
- $R_{11}$ is hydrogen, $C_1$–$C_4$alkyl or halo-$C_1$–$C_4$alkyl; and
- $R_{12}$ is $C_1$–$C_4$alkyl, halo-$C_1$–$C_4$alkyl, unsubstituted phenyl or mono- or di-substituted phenyl, the substituents being selected from the group consisting of halogen, $C_1$–$C_4$alkyl, halo-$C_1$–$C_4$alkyl, $C_1$–$C_4$alkoxy, halo-$C_1$–$C_4$alkoxy, $C_1$–$C_4$alkylthio, halo-$C_1$–$C_4$alkylthio, —$NO_2$ and —CN;

and, where appropriate, tautomers thereof, and the salts thereof and the salts of the tautomers;

with the proviso (A) that, in compounds of formula I in free form wherein each of o and p is 0, $R_4$ is hydrogen and X is N, $R_3$ is other than hydrogen when $R_5$ is methanesulfonyl, unsubstituted phenylsulfonyl or 4-methylphenylsulfonyl and with the further proviso (B) that, in compounds of formula I in free form wherein each of o and p is 1, $R_1$ is methanesulfonyloxy, $R_2$ is chlorine, $R_4$ is methyl, X is C($R_9$) and $R_9$ is hydrogen, $R_3$ is other than hydrogen when $R_5$ is ethoxycarbonyl, methoxycarbonyl or cyano;

to a process for the preparation of those compounds and tautomers, to the use of those compounds and tautomers, to pesticidal compositions the active ingredient of which is selected from those compounds and tautomers, or the agrochemically acceptable salts thereof, and to a process for the preparation of those compositions and to the use of those compositions.

Some of the compounds of formula I may be in the form of tautomers. When, for example, $R_3$ is hydrogen and X is N, corresponding compounds of formula I, that is to say, those having a —N(H)—C($R_4$)=N—$R_5$ partial structure, may be in equilibrium with the relevant tautomers which have a —N=C($R_4$)—N(H)—$R_5$ partial structure. Hereinafter, therefore, the compounds of formula I are, where appropriate, also to be understood as being corresponding tautomers, even when the latter are not mentioned specifically in every case.

The compounds of formula I and, where appropriate, their tautomers may be in the form of salts. Compounds of formula I that have at least one basic centre can, for example, form acid addition salts. These are formed, for example, with strong inorganic acids, such as mineral acids, for example sulfuric acid, a phosphoric acid or a hydrohalic acid, with strong organic carboxylic acids, such as unsubstituted or substituted, for example halo-substituted, $C_1$–$C_4$alkanecarboxylic acids, for example acetic acid, saturated or unsaturated dicarboxylic acids, for example oxalic, malonic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halo-substituted, $C_1$–$C_4$alkane- or aryl-sulfonic acids, for example methane- or p-toluene-sulfonic acid. In addition, compounds of formula I having at least one acidic group can form salts with bases. Suitable salts with bases are, for example, metal salts, such as alkali metal or alkaline earth metal salts, for example sodium, potassium or magnesium salts, or salts with ammonia or an organic amine, such as morpholine, piperidine, pyrrolidine, a mono-, di- or trilower alkylamine, for example ethyl-, diethyl-, triethyl- or dimethyl-propyl-amine, or a mono-, di- or tri-hydroxy-lower alkylamine, for example mono-, di- or tri-ethanolamine. Furthermore, corresponding internal salts may possibly be formed. Within the scope of the invention agrochemically advantageous salts are preferred; however, salts that have disadvantages with respect to agrochemical uses but which can be used, for example, for the isolation or purification of free compounds of formula I or the agrochemically acceptable salts thereof are also included. Hereinbefore and hereinafter, therefore, the expression "compound of formula I" also includes the salts of those compounds, the tautomers of those compounds and the salts of the tautomers.

Halogen—as a substituent per se and also as a structural element of other groups and compounds, such as of haloalkyl, haloalkoxy, haloalkylthio, halomethylene and haloeth-1,2-ylene,—is fluorine, chlorine, bromine or iodine, especially fluorine, chlorine or bromine, more especially fluorine or chlorine.

Carbon-containing groups and compounds contain, unless otherwise defined, in each case from 1 up to and including 8, preferably from 1 up to and including 4, especially 1 or 2, carbon atoms.

$C_3$-$C_6$cycloalkyl is cyclopropyl, cyclobutyl, cyclopentyl or cyclohexyl.

Alkyl—as a group per se and also as a structural element of other groups and compounds, such as of haloalkyl, alkoxy, haloalkoxy, alkylthio and haloalkylthio,—is, in each case with due consideration of the included number of carbon atoms contained in the corresponding group or compound, either straight-chained, that is to say, methyl, ethyl, propyl, butyl, pentyl, hexyl, heptyl or octyl, or branched, for example isopropyl, isobutyl, sec-butyl, tert-butyl, isopentyl, neopentyl or isooctyl.

Halo-substituted carbon-containing groups and compounds, such as haloalkyl, haloalkoxy, haloalkylthio, halomethylene and haloeth-1,2-ylene, may be partially halogenareal or perhalogenated, and in the case of polyhalogenation the halogen substituents may be the same or different. Examples of haloalkyl—as a group per se and also as a structural element of other groups and compounds, such as of haloalkylthio and haloalkoxy—are methyl mono- to tri-substituted by fluorine, chlorine and/or by bromine, such as $CHF_2$ or $CF_3$; ethyl mono- to penta-substituted by fluorine, chlorine and/or by bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl mono- to hepta-substituted by fluorine, chlorine and/or by bromine, such as $CH_2CHBrCH_2Br$, $CF_2CHFCF_3$, $CH_2CF_2CF_3$ or $CH(CF_3)_2$; and butyl, or one of its isomers, mono- to nona-substituted by fluorine, chlorine and/or by bromine, such as $CF(CF_3)CHFCF_3$ or $CH_2(CF_2)_2CF_3$. Examples of halomethylene are fluoromethylene, difluoromethylene and dichloromethylene. Examples of haloeth-1,2ylene are 1,2-difluoroeth-1,2-ylene, tetrafluoroeth-1,2-ylene and tetrachloroeth-1,2-ylene.

Preferred forms within the scope of the invention, in each case taking into account the above-mentioned provisos (A) and (B), are:

(1) A compound of formula I wherein
each of o and p, independently of the other, is 0, 1, 2, 3, 4 or 5, the radicals $R_1$ being the same or different when o is greater than 1 and the radicals $R_2$ being the same or different when p is greater than 1; each of $R_1$ and $R_2$, independently of the other, is $C_1$-$C_4$alkyl, halo-$C_1$-$C_4$alkyl, halogen, —OH, $C_1$-$C_4$alkoxy, halo-$C_1$-$C_4$alkoxy, $C_1$-$C_4$alkylthio, halo-$C_1$-$C_4$alkylthio, —O—S(=O)—$R_6$ or —O—S(=O)$_2$—$R_6$ and/or two substituents $R_1$ bonded to vicinal carbon atoms of the phenyl ring and/or two substituents $R_2$ bonded to vicinal carbon atoms of the phenyl ring are, independently of one another, together —Y—Z—Y—;
$R_3$ is hydrogen, $C_1$-$C_4$alkyl or halo-$C_1$-$C_4$alkyl;
$R_4$ is hydrogen, $C_1$-$C_4$alkyl, halo-$C_1$-$C_4$alkyl, unsubstituted phenyl or naphthyl or mono-or di-substituted phenyl or naphthyl, the substituents being selected from the group consisting of halogen, $C_1$-$C_4$alkyl, halo-$C_1$-$C_4$alkyl, $C_1$-$C_4$alkoxy, halo-$C_1$-$C_4$alkoxy, $C_1$-$C_4$alkylthio, halo-$C_1$-$C_4$alkylthio, —$NO_2$ and —CN;
$R_5$ is —S—$R_7$, —S(=O)—$R_7$, —S(=0)$_2$—$R_7$, —$NO_2$, —CN, —C(=O)—$R_8$ or —C(=O)—$OR_8$;
$R_6$ is $C_1$-$C_8$alkyl or halo-$C_1$-$C_8$alkyl;
$R_7$ is $C_1$-$C_8$alkyl, $C_3$-$C_6$cycloalkyl, halo-$C_1$-$C_8$alkyl or unsubstituted or mono- or disubstituted phenyl, the substituents being selected from the group consisting of halogen, $C_1$-$C_4$alkyl, halo-$C_1$-$C_4$alkyl, $C_1$-$C_4$alkoxy, halo-$C_1$-$C_4$alkoxy, $C_1$-$C_4$alkylthio, halo-$C_1$-$C_4$alkylthio, —$NO_2$ and —CN;
$R_8$ is $C_1$-$C_8$alkyl, halo-$C_1$-$C_8$alkyl or unsubstituted or mono- or di-substituted phenyl, the substituents being selected from the group consisting of halogen, $C_1$-$C_4$alkyl, halo-$C_1$-$C_4$alkyl, $C_1$-$C_4$alkoxy, halo-$C_1$-$C_4$alkoxy, $C_1$-$C_4$alkylthio, halo-$C_1$-$C_4$alkylthio, —$NO_2$ and —CN;
X is N or C($R_9$);
each Y, independently of the other, is O or S;
Z is methylene, eth-1,2-ylene, halomethylene or haloeth-1,2-ylene;
$R_9$ is hydrogen, $C_1$-$C_4$alkyl, halo-$C_1$-$C_4$alkyl, —CN, —C(=O)-$R_{10}$ or —C(=O)—$OR_{10}$; and
$R_{10}$ is $C_1$-$C_8$alkyl or halo-$C_1$-$C_8$alkyl;
and, where appropriate, tautomers thereof;

(2) A compound of formula I wherein o is 1 or 2, the radicals $R_1$ being the same or different when o is 2, and
$R_1$ is halogen, —$NO_2$, —OH, —O—S(=O)$_2$-$C_1$-$C_4$alkyl, —O—S(=O)$_2$-halo-$C_1$-$C_4$alkyl, phenoxy, —$NO_2$ or —N($R_{11}$)$SO_2R_{12}$ or two substituents $R_1$ bonded to vicinal carbon atoms of the phenyl ring are together —O-methylene-O— or —O-halomethylene-O—, $R_{11}$ is hydrogen or $C_1$-$C_4$alkyl, and $R_{12}$ is halo-$C_1$-$C_4$alkyl; especially wherein $R_1$ is halogen, —OH, —O—S(=O)$_2$-$C_1$-$C_4$alkyl, —O—S(=O)$_2$-halo-$C_1$-$C_4$alkyl, phenoxy or —N($R_{11}$)$SO_2$-halo-$C_1$-$C_2$alkyl or two substituents $R_1$ bonded to vicinal carbon atoms of the phenyl ring are together —O-methylene-O— or —O-halomethylene-O— and $R_{11}$ is hydrogen or $C_1$-$C_2$alkyl;

very especially o is 1 or 2, the radicals $R_1$ being the same when o is 2, and $R_1$ is halogen, —OH, —O—S(=O)$_2$-$C_1$-$C_2$alkyl, —O—S(=O)$_2$-halo-$C_1$-$C_2$alkyl or —N($C_2H_5$)$SO_2CF_3$ or two substituents $R_1$ bonded to vicinal carbon atoms of the phenyl ring are together —O -halomethylene—O—;
more especially ($R_1$)$_o$ is 4-trifluoromethanesulfonyloxy, 4-methanesulfonyloxy, or is —$OCF_2O$— bonded in the 3- and 4-positions;
especially preferably ($R_1$)$_o$ is 4-trifluoromethanesulfonyloxy, or, where appropriate, a tautomer thereof;

(3) A compound of formula I wherein p is 0, 1 or 2, the radicals $R_2$ being the same or different when p is 2, and
$R_2$ is halogen, —OH, —O—S(=O)$_2$-$C_1$-$C_4$alkyl or —O—S(=O)$_2$-halo-$C_1$-$C_4$alkyl or two substituents $R_2$ bonded to vicinal carbon atoms of the phenyl ring are together —O -methylene-O— or —O-halomethylene-O—;

especially p is 0, 1 or 2, the radicals $R_2$ being the same when p is 2, and $R_2$ is halogen, —OH, —O—S(=O)$_2$—C$_1$-C$_2$alkyl or —O—S(=O)$_2$-halo-C$_1$-C$_2$alkyl or two substituents $R_2$ bonded to vicinal carbon atoms of the phenyl ring are together —O— halomethylene-O—;

more especially $(R_2)_p$ is fluorine, chlorine, bromine or $C_1$-$C_4$alkyl;

very especially $(R_2)_p$ is 2-chloro, 4-chloro, 2,4-dichloro, 3,4-dichloro or 4-fluoro;

very especially preferably 4-chloro, or, where appropriate, a tautomer thereof;

(4) A compound of formula I wherein
$R_3$ is hydrogen or $C_1$-$C_4$alkyl;
especially hydrogen or $C_1$-$C_2$alkyl;
more especially hydrogen or methyl;
very especially hydrogen, or, where appropriate, a tautomer thereof;

(5) A compound of formula I wherein
$R_4$ is hydrogen, $C_1$-$C_4$alkyl, halo-$C_1$-$C_4$alkyl or phenyl;
especially hydrogen, $C_1$-$C_2$alkyl, halo-$C_1$-$C_2$alkyl or phenyl;
more especially hydrogen or methyl;
very especially hydrogen, or, where appropriate, a tautomer thereof;

(6) A compound of formula I wherein
$R_5$ is —S(=O)$_2$—R$_7$, —CN, —C(=O)—R$_8$ or —C(=O)—OR$_8$,
$R_7$ is $C_1$-$C_6$alkyl, $C_3$-$C_6$cycloalkyl, halo-$C_1$-$C_4$alkyl, benzyl, $C_1$-$C_4$dialkylamino, or phenyl that is unsubstituted or mono-substituted by halogen, $C_1$-$C_4$alkyl or by $C_1$-$C_4$alkoxy,
$R_8$ is $C_1$-$C_4$alkyl, halo-$C_1$-$C_4$alkyl or phenyl,
X is N or C($R_9$),
$R_9$ is hydrogen, —CN or —C(=O)—OR$_{10}$ and $R_{10}$ is $C_1$-$C_4$alkyl; especially
$R_5$ is —S(=O)$_2$—R$_7$, —CN, —C(=O)—R$_8$ or —C(=O)—OR$_8$,
$R_7$ is $C_1$-$C_4$alkyl, halo-$C_1$-$C_2$alkyl, benzyl or dimethylamino, or phenyl that is unsubstituted or mono-substituted by halogen, $C_1$-$C_2$alkyl or by $C_1$-$C_2$alkoxy,
$R_8$ is $C_1$-$C_4$alkyl or halo-$C_1$-$C_2$alkyl,
X is N or C($R_9$), $R_9$ is hydrogen, —CN or —C(=O)—OR$_{10}$ and $R_{10}$ is $C_1$-$C_4$alkyl; more especially
$R_5$ is —S(=O)$_2$—R$_7$, —CN or —C(=O)—R$_8$,
$R_7$ is $C_1$-$C_4$alkyl, chloromethyl, bromomethyl, or phenyl that is unsubstituted or mono-substituted in the 4-position by halogen, $C_1$-$C_2$alkyl or by $C_1$-$C_2$alkoxy, or is benzyl or dimethylamino,
$R_8$ is methyl or trifluoromethyl,
X is N or C($R_9$) and
$R_9$ is hydrogen, or, where appropriate, a tautomer thereof;

(7) A compound of formula I wherein
o is 1 or 2,
p is 0, 1 or 2, the radicals $R_1$ being the same or different when O is 2 and the radicals $R_2$ being the same or different when p is 2;
each of $R_1$ and $R_2$, independently of the other, is halogen, —NO$_2$, —OH, phenoxy, —N($R_{11}$)SO$_2$CF$_3$ or —O—S(=O)$_2$—R$_6$ or two substituents $R_1$ bonded to vicinal carbon atoms of the phenyl ring or two substituents $R_2$ bonded to vicinal carbon atoms of the phenyl ring are together —O—Z—O—;

$R_3$ is hydrogen or $C_1$-$C_4$alkyl;
$R_4$ is hydrogen, $C_1$-$C_4$alkyl, halo-$C_1$-$C_4$alkyl or unsubstituted phenyl;
$R_5$ is —S(=O)$_2$—R$_7$, —CN, —C(=O)—R$_8$ or —C(=O)—OR$_8$;
$R_6$ is $C_1$-$C_4$alkyl, halo-$C_1$-$C_4$alkyl or phenyl;
$R_7$ is $C_1$-$C_6$alkyl, $C_3$-$C_6$cycloalkyl, halo-$C_1$-$C_4$alkyl, phenyl that is unsubstituted or mono-substituted by halogen, $C_1$-$C_4$alkyl or by $C_1$-$C_4$alkoxy, or is benzyl or dimethylamino;
$R_8$ is $C_1$-$C_4$alkyl or halo-$C_1$-$C_4$alkyl;
X is N or C($R_9$);
Z is methylene or halomethylene;
$R_9$ is hydrogen, —CN, —C(=O)—R$_{10}$ or —C(=O)—OR$_{10}$;
$R_{10}$ is $C_1$-$C_4$alkyl and
$R_{11}$ is hydrogen, methyl or ethyl, or, where appropriate, a tautomer thereof;

(8) A compound of formula I wherein
o is 1 or 2,
p is 0, 1 or 2, the radicals $R_1$ being the same or different when O is 2 and the radicals $R_2$ being the same or different when p is 2;
each of $R_1$ and $R_2$, independently of the other, is halogen, —OH or —O—S(=O)$_2$—R$_6$ or two substituents $R_1$ bonded to vicinal carbon atoms of the phenyl ring or two substituents $R_2$ bonded to vicinal carbon atoms of the phenyl ring are together —O—Z—O—;
$R_3$ is hydrogen or $C_1$-$C_4$alkyl;
$R_4$ is hydrogen, $C_1$-$C_4$alkyl, halo-$C_1$-$C_4$alkyl or unsubstituted phenyl;
$R_5$ is —S(=O)$_2$—R$_7$, —CN, —C(=O)—R$_8$ or —C(=O)—OR$_8$;
$R_6$ is $C_1$-$C_4$alkyl or halo-$C_1$-$C_4$alkyl;
$R_7$ is $C_1$-$C_6$alkyl, $C_3$-$C_6$cycloalkyl, halo-$C_1$-$C_4$alkyl, or phenyl that is unsubstituted or mono-substituted by halogen, $C_1$-$C_4$alkyl or by $C_1$-$C_4$alkoxy, or is benzyl or dimethylamino;
$R_8$ is $C_1$-$C_4$alkyl or halo-$C_1$-$C_4$alkyl;
X is N or C($R_9$);
Z is methylene or halomethylene;
$R_9$ is hydrogen, —CN, —C(=O)—R$_{10}$ or —C(=O)—OR$_{10}$; and
$R_{10}$ is $C_1$-$C_4$alkyl, or, where appropriate, a tautomer thereof;

(9) A compound of formula I wherein
o is 1 or 2,
p is 0, 1 or 2, the radicals $R_1$ being the same when o is 2 and the radicals $R_2$ being the same when p is 2;
each of $R_1$ and $R_2$, independently of the other, is halogen, —OH or —O—S(=O)$_2$—R$_6$ or two substituents $R_1$ bonded to vicinal carbon atoms of the phenyl ring or two substituents $R_2$ bonded to vicinal carbon atoms of the phenyl ring are together —O—Z—O—;
$R_3$ is hydrogen or $C_1$-$C_2$alkyl;
$R_4$ is hydrogen, $C_1$-$C_2$alkyl, halo-$C_1$-$C_2$alkyl or unsubstituted phenyl;
$R_5$ is —S(=O)$_2$—R$_7$, —CN, —C(=O)—R$_8$ or —C(=O)—OR$_8$;
$R_6$ is $C_1$-$C_2$alkyl or halo-$C_1$-$C_2$alkyl;
$R_7$ is $C_1$-$C_4$alkyl, halo-$C_1$-$C_2$alkyl, or phenyl that is unsubstituted or mono-substituted by halogen, $C_1$-$C_2$alkyl or by $C_1$-$C_2$alkoxy;
$R_8$ is $C_1$-$C_4$alkyl or halo-$C_1$-$C_2$alkyl;
X is N or C($R_9$);
Z is halomethylene;

$R_9$ is hydrogen, —CN or —C(=O)—OR$_{10}$; and
$R_{10}$ is $C_1$-$C_2$alkyl, or, where appropriate, a tautomer thereof;

(10) A compound of formula I wherein
($R_1$)$_o$ is 4-trifluoromethanesulfonyloxy, 4-methanesulfonyloxy, or is —OCF$_2$O— bonded in the 3- and 4-positions;
$R_2$ is fluorine, chlorine, bromine or $C_1$-$C_4$alkyl;
$R_3$ is hydrogen;
$R_4$ is hydrogen or methyl;
$R_5$ is —S(=O)$_2$—R$_7$;
$R_7$ is $C_1$-$C_4$alkyl, chloromethyl, bromomethyl, or phenyl that is unsubstituted or mono-substituted in the 4-position by halogen, $C_1$-$C_2$alkyl or by $C_1$-$C_2$alkoxy; and
X is N, or, where appropriate, a tautomer thereof;

(11) A compound of formula I wherein
($R_1$)$_o$ is 4-trifluoromethanesulfonyloxy;
($R_2$)$_p$ is 2-chloro, 4-chloro, 2,4-dichloro, 3,4-dichloro or 4-fluoro;
$R_3$ is hydrogen;
$R_4$ is methyl or trifluoromethyl;
$R_5$ is —CN or —C(=O)—R$_8$;
$R_8$ is methyl or trifluoromethyl;
X is C($R_9$); and
$R_9$ is hydrogen or —CN, or, where appropriate, a tautomer thereof.

Especially preferred within the scope of the invention are the compounds of formula I mentioned in Examples P1 to P3 and, where appropriate, the tautomers thereof.

Specifically preferred within the scope of the invention are
(a) 1-(4-chlorophenyl)-5-ethanesulfonyl-2,3,5-triaza-1-(4-trifluoromethanesulfonyloxy-phenyl)-penta-1,4-diene and 1-(4-chlorophenyl)-5-ethanesulfonyl-2,3,5-triaza-1-(4-trifluoromethanesulfonyloxy-phenyl)-penta-1,3-diene; and
(b) 1-(4-chlorophenyl)-2,3-diaza-4-methyl-6-oxo-1-(4-trifluoromethanesulfonyloxyphenyl)-hepta-1,4-diene and 1-(4-chlorophenyl)-2,3-diaza-4-methyl-6-oxo-1-(4-trifluoromethanesulfonyloxyphenyl)-hepta-1,3-diene.

Taking into account the above-mentioned provisos (A) and (B), the invention relates also to a process for the preparation of the compounds of formula I and, where appropriate, the tautomers thereof, in each case in free form or in salt form, wherein, for example,
a) a compound of the formula

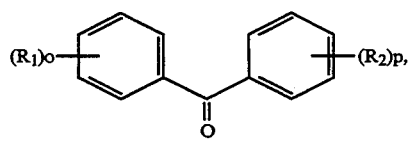

wherein o, p, $R_1$ and $R_2$ are as defined for formula I, is reacted, preferably in the presence of an acid, with a compound of the formula

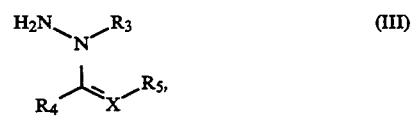

wherein $R_3$, $R_4$, $R_5$ and X are as defined for formula I, or with a salt and/or, where appropriate, with a tautomer thereof, or
b) a compound of the formula

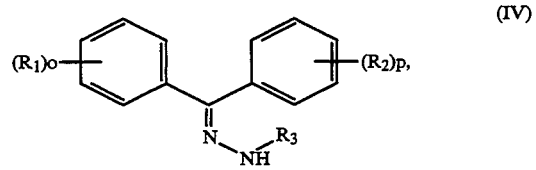

wherein o, p, $R_1$, $R_2$ and $R_3$ are as defined for formula I, or a salt thereof, is reacted, preferably in the presence of an acid or base, with a compound of the formula

wherein L is hydroxy, $C_1$-$C_8$alkoxy, halo-$C_1$-$C_8$alkoxy, $C_1$-$C_8$alkanoyloxy, mercapto, $C_1$-$C_8$alkylthio, halo-$C_1$-$C_8$alkylthio, $C_1$-$C_8$alkanesulfonyloxy, halo-$C_1$-$C_8$alkanesulfonyloxy, benzenesulfonyloxy, toluenesulfonyloxy or halogen and $R_4$, $R_5$ and X are as defined for formula I, or with a salt and/or, where appropriate, with a tautomer thereof, and, in each case, if desired, a compound of formula I obtainable in accordance with the process or in another manner or a tautomer thereof, or, where appropriate, a salt of the compound or tautomer, is converted into a different compound of formula I or a tautomer thereof, a mixture of isomers obtainable in accordance with the process is separated and the desired isomer is isolated and/or a free compound of formula I obtainable in accordance with the process or a tautomer thereof is converted into a salt or a salt, obtainable in accordance with the process, of a compound of formula I or of a tautomer thereof is converted into the free compound of formula I or a tautomer thereof or into a different salt.

The statements made hereinbefore in connection with tautomers and salts of compounds of formula I apply analogously to the tautomers and salts of the starting materials indicated hereinbefore and hereinafter.

The reactions described hereinbefore and hereinafter are carried out in a manner known per se, for example in the absence or, generally, in the presence of a suitable solvent or diluent or a mixture thereof, the operation being carried out, as required, with cooling, at room temperature or with heating, for example in a temperature range of approximately from −80° C. up to the boiling temperature of the reaction medium, preferably from approximately −20° C. to approximately +150° C., and, if necessary, in a closed vessel, under pressure, in an inert gas atmosphere and/or under anhydrous conditions. Especially advantageous reaction conditions can be found in the Examples.

The starting materials indicated hereinbefore and hereinafter, which are used for the preparation of the compounds of formula I and, where appropriate, the tautomers thereof, in each case in free form or in salt form, are known or can be prepared in accordance with methods known per se, for example in accordance with the following.

Variant a):

Suitable acids for facilitating condensation are, for example, those indicated above as being suitable for the formation of acid addition salts with compounds of formula I.

The reactants can be reacted with one another as such, that is to say, without the addition of a solvent or diluent, for example in the melt. Generally, however, the addition of an inert solvent or diluent or a mixture thereof is advantageous. There may be mentioned as examples of such solvents and diluents: aromatic, aliphatic and alicyclic hydrocarbons and halogenated hydrocarbons, such as benzene, toluene, xylene, chlorobenzene, bromobenzene, petroleum ether, hexane, cyclohexane, dichloromethane, trichloromethane, dichloroethane or trichloroethane; esters, such as ethyl acetate; ethers, such as diethyl ether, tert-butyl methyl ether, ethylene glycol monomethyl ether, ethylene glycol monoethyl ether, ethylene glycol dimethyl ether, tetrahydrofuran or dioxane; ketones, such as acetone, methyl ethyl ketone or methyl isobutyl ketone; alcohols, such as methanol, ethanol, propanol, butanol, ethylene glycol or glycerol; amides, such as N,N-dimethylformamide, N,N-dimethylacetamide, N-methylpyrrolidone or hexamethylphosphoric acid triamide; nitriles, such as acetonitrile; sulfoxides, such as dimethyl sulfoxide; and acids, for example strong organic carboxylic acids, such as unsubstituted or substituted, for example halo-substituted, $C_1$–$C_4$alkanecarboxylic acids, for example formic acid, acetic acid or propionic acid.

The reaction is advantageously carried out in a temperature range of from approximately 0° C. to approximately +180° C., preferably from approximately +20° C. to approximately +130° C., in many cases at the reflux temperature of the solvent used.

The compounds of formula II and the compounds of formula III and, where appropriate, the tautomers thereof and also the salts of the compounds and tautomers are known or can be prepared analogously to known compounds.

Variant b:

Suitable acids for facilitating HL-removal are, for example, those indicated above as being suitable for the formation of acid addition salts with compounds of formula I.

Suitable bases for facilitating HL-removal are, for example, alkali metal or alkaline earth metal hydroxides, hydrides, amides, alkanolates, carbonates, dialkylamides or alkylsilylamides; alkylamines, alkylenediamines, unsubstituted or N-alkylated, unsaturated or saturated cycloalkylamines, basic heterocycles, ammonium hydroxides and carbocyclic amines. There may be mentioned by way of example: sodium hydroxide, hydride, amide, methanolate and carbonate, potassium tert-butanolate and carbonate, lithium diisopropylamide, potassium bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)pyridine, N-methylmorpholine, benzyltrimethylammonium hydroxide and also 1,5-diazabicyclo[5.4.0]undec-5-ene (DBU).

The reactants can be reacted with one another as such, that is to say without the addition of a solvent or diluent, for example in the melt. Generally, however, the addition of an inert solvent or diluent or a mixture thereof is advantageous. There may be mentioned as examples of such solvents and diluents: aromatic, aliphatic and alicyclic hydrocarbons and halogenated hydrocarbons, such as benzene, toluene, xylene, chlorobenzene, bromobenzene, petroleum ether, hexane, cyclohexane, dichloromethane, trichloromethane, dichloroethane or trichloroethane; esters, such as ethyl acetate; ethers, such as diethyl ether, tert-butyl methyl ether, ethylene glycol monomethyl ether, ethylene glycol monoethyl ether, ethylene glycol dimethyl ether, tetrahydrofuran or dioxane; ketones, such as acetone, methyl ethyl ketone or methyl isobutyl ketone; alcohols, such as methanol, ethanol, propanol, butanol, ethylene glycol or glycerol; amides, such as N,N-dimethylformamide, N,N-dimethylacetamide, N-methylpyrrolidone or hexamethylphosphoric acid triamide; nitriles, such as acetonitrile; and sulfoxides, such as dimethyl sulfoxide. If the reaction is carried out in the presence of an acid, it is possible for acids used in excess, for example strong organic carboxylic acids, such as unsubstituted or substituted, for example halo-substituted, $C_1$–$C_4$alkanecarboxylic acids, for example formic acid, acetic acid or propionic acid, to serve also as solvent or diluent. If the reaction is carried out in the presence of a base it is possible for bases used in excess, such as triethylamine, pyridine, N-methylmorpholine or N,N-diethylaniline, to serve also as solvent or diluent.

The reaction is advantageously carried out in a temperature range of from approximately −20° C. to approximately +180° C., preferably from approximately 0° C. to approximately +120° C., in many cases at the reflux temperature of the solvent used.

In a preferred form of variant b), a compound (IV) is reacted at reflux temperature in an ether, preferably in dioxane, and in the presence of an alkylamine, preferably in the presence of triethylamine, with a compound (V) wherein L is alkoxy.

In a further preferred form of variant b), a compound (IV) is reacted at reflux temperature in an aromatic hydrocarbon, preferably in toluene, and in the presence of an organic carboxylic acid, preferably in the presence of acetic acid, with a compound (V) wherein L is hydroxy, or with a tautomer thereof.

The compounds of formula IV and the salts thereof, and also the compounds of formula V and, where appropriate, the tautomers thereof, in each case in free form or in salt form, are known or can be prepared analogously to known compounds.

A compound I obtainable in accordance with the process or in another manner or, where appropriate, a tautomer thereof can be converted in a manner known per se into a different compound I by replacing one or more substituents of the starting compound I in customary manner by (an)other substituent(s) according to the invention.

For example:

hydroxy groups $R_1$ and/or $R_2$ can be alkylated to $C_1$–$C_4$alkoxy groups $R_1$ and/or $R_2$;

halogen $R_1$ and/or $R_2$ can be introduced into unsubstituted positions of the phenyl ring(s) concerned; or mercapto groups $R_5$ can be oxidised to sulfinyl or sulfonyl groups $R_5$, or sulfinyl groups $R_5$ can be oxidised to sulfonyl groups $R_5$.

In that conversion it is possible, depending on the chosen starting materials and reaction conditions suitable for the particular purpose, to replace, in one reaction step, only one substituent by another substituent according to the invention, or it is possible in the same reaction step to replace several substituents by other substituents according to the invention.

Salts of compounds of formula I can be prepared in a manner known per se. For example, acid addition salts of compounds of formula I are obtained by treatment with a suitable acid or with a suitable ion-exchange reagent, and salts with bases can be obtained by treatment with a suitable base or a suitable ion-exchange reagent.

Salts of compounds of formula I can be converted in customary manner into the free compounds of formula I; for example, acid addition salts can be converted by treatment with a suitable basic agent or a suitable ion-exchange reagent, and salts with bases, for example, by treatment with a suitable acid or a suitable ion-exchange reagent.

Salts of compounds of formula I can be converted in a manner known per se into other salts of compounds of formula I; for example, acid addition salts can be converted into other acid addition salts, for example by treating a salt of an inorganic acid, such as a hydrochloride, with a suitable metal salt, such as a sodium, barium or silver salt, of an acid, for example with silver acetate, in a suitable solvent in which an inorganic salt being formed, for example silver chloride, is insoluble and is thus eliminated from the reaction mixture.

Depending on the procedure and reaction conditions, the compounds of formula I having salt-forming properties can be obtained in free form or in the form of salts.

The compounds of formula I and, where appropriate, the tautomers thereof, in each case in free form or in salt form, may be in the form of one of the possible isomers or in the form of a mixture thereof; for example, depending on the number and absolute and relative configuration of asymmetric carbon atoms occurring in the molecule and/or depending on the configuration of non-aromatic double bonds occurring in the molecule, they may be in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and is to be understood accordingly hereinbefore and hereinafter, even when stereochemical details are not specifically mentioned in every case.

Mixtures of diastereoisomers and mixtures of racemates, obtainable in accordance with the processes—depending on the starting materials and procedures chosen—or obtainable in another manner, of compounds of formula I and, where appropriate, of the tautomers thereof, in each case in free form or in salt form, can be separated into the pure diastereoisomers or racemates on the basis of the physico-chemical differences between the constituents in known manner, for example by fractional crystallisation, distillation and/or chromatography.

Correspondingly obtainable mixtures of enantiomers, such as racemates, can be resolved into the optical antipodes in accordance with known methods, for example by recrystallisation from an optically active solvent, by chromatography on chiral adsorbents, for example high pressure liquid chromatography (HPLC) on acetylcellulose, using suitable micro-organisms, by cleavage with specific immobilised enzymes, by means of the formation of inclusion compounds, for example using chiral crown ethers, only one enantiomer being complexed, or by conversion into diastereoisomeric salts, for example by reaction of a basic end product racemate with an optically active acid, such as a carboxylic acid, for example camphoric, tartaric or malic acid, or a sulfonic acid, for example camphorsulfonic acid, and separation of the mixture of diastereoisomers so obtained, for example on the basis of their different solubilities by fractional crystallisation, into the diastereoisomers from which the desired enantiomer can be freed by the action of suitable, for example basic, agents.

Apart from by separating corresponding mixtures of isomers, pure diastereoisomers and enantiomers can also be obtained according to the invention by generally known methods of diastereoselective and enantioselective synthesis, respectively, for example by carrying out the process according to the invention with educts having correspondingly suitable stereochemistry.

Advantageously, the biologically more active isomer, for example enantiomer or diastereoisomer, or mixture of isomers, for example a mixture of enantiomers or a mixture of diastereoisomers, is isolated or synthesised, if the individual components have different biological activities.

The compounds of formula I and, where appropriate, the tautomers thereof, in each case in free form or in salt form, can also be obtained in the form of their hydrates and/or may include other solvents, for example solvents that are used, where appropriate, for the crystallisation of compounds that are in solid form.

The invention relates to all those forms of the process according to which a compound obtainable as starting material or intermediate at any stage of the process is used as starting material and all or some of the remaining steps are carried out or a starting material is used in the form of a derivative or salt and/or its racemates or antipodes or, especially, is formed under the reaction conditions.

In the process of the present invention, it is preferable to use those starting materials and intermediates or the salts thereof that result in the compounds of formula I or the salts thereof described in the introduction as being especially valuable.

The invention relates especially to the preparation processes described in Examples 1 to P3.

The invention relates also to those starting materials and intermediates or the salts thereof that are novel and which are used according to the invention for the preparation of the compounds of formula I or the salts thereof, to their use and to processes for the preparation thereof.

The compounds of formula I according to the invention are valuable active ingredients in the field of pest control, while being well tolerated by warm-blooded animals, fish and plants, the above-mentioned proviso (A) not applying to these active ingredients. The compounds according to the invention are effective especially against insects that occur on useful plants and ornamentals in agriculture and horticulture, especially in cotton, vegetable and fruit crops, and in forestry. The compounds according to the invention are suitable especially for the control of insects in fruit and vegetable crops, especially for the control of plant-destructive insects, such as *Spodoptera littoralis, Heliothis virescens, Diabrotica balteata* and *Crocidolomia binotalis*. Other fields of application for the compounds according to the invention are the protection of stored goods and materials, and also in the hygiene sector, especially the protection of domestic animals and productive livestock. The compounds according to the invention are effective against all or individual stages of development of normally sensitive and also resistant species of pests. Their action may, for example, cause the pests to die immediately or only after some time, for example during moulting, or it may manifest itself in a reduced oviposition and/or hatching rate.

The above-mentioned pests include:

from the order of the Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis*, Chilo spp., Choristoneura spp., *Clysia ambiguella*, Cnaphalocrocis spp., Cnephasia spp., Cochylis spp., Coleophora spp., *Crocidolomia binotalis, Cryptophlebia leucotreta*, Cydia spp., Diatraea spp., *Diparopsis castanea*, Earias spp., Ephestia spp., Eucosma spp., *Eupoecilia ambiguella*, Euproctis spp., Euxoa spp., Grapholita spp., *Hedya nubiferana*, Heliothis spp., *Hellula undalis, Hyphantria cunea, Keiferia lycopersicella, Leucoptera scitella*, Lithocollethis spp., *Lobesia botrana*, Lymantria spp., Lyonetia spp., Malacosoma spp., *Mamestra brassicae, Manduca sexta*, Operophtera spp., *Ostrinia nubilalis*, Pammene spp., Pandemis spp., *Panolis flammea, Pectinophora gossypiella, Phthorimaea operculella, Pieris rapae*, Pieris spp., *Plutella xylostella*, Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order of the Coleoptera, for example Agriotes spp., Anthonomus spp., *Atomaria linearis, Chaetocnema tibialis*, Cosmopolites spp., Curculio spp., Dermestes spp., Diabrotica spp., Epilachna spp., Eremnus spp., *Leptinotarsa decemlineata*, Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order of the Orthoptera, for example Blatta spp., Blattella spp., Gryllotalpa spp., *Leucophaea maderae*, Locusha spp., Periplaneta spp. and Schistocerca spp.;

from the order of the Isoptera, for example Reticulitermes spp.;

from the order of the Psocoptera, for example Liposcelis spp.;

from the order of the Anoplura, for example Haematopinus spp., Linognathus spp., Pediculus spp., Pemphigus spp. and Phylloxera spp.;

from the order of the Mallophaga, for example Damalinea spp. and Trichodectes spp.;

from the order of the Thysanoptera, for example Frankliniella spp., Hercinothrips spp., Taeniothrips spp., *Thrips palmi, Thrips tabaci* and *Scirtothrips aurantii*;

from the order of the Heteroptera, for example Cimex spp., *Distantiella theobroma*, Dysdercus spp., Euchistus spp. Eurygaster spp. Leptocorisa spp., Nezara spp., Piesma spp., Rhodnius spp., *Sahlbergella singularis*, Scotinophara spp. and Triatoma spp.;

from the order of the Homoptera, for example *Aleurothrixus floccosus, Aleyrodes brassicae*, Aonidiella spp., Aphididae, Aphis spp., Aspidiotus spp., *Bemisia tabaci*, Ceroplaster spp., *Chrysomphalus aonidium, Chrysomphalus dictyospermi, Coccus hesperidum*, Empoasca spp., *Eriosoma larigerum*, Erythroneura spp., Gascardia spp., Laodelphax spp., *Lecanium corni*, Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica*, Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri*;

from the order of the Hymenoptera, for example Acromyrmex, Alta spp., Cephus spp., Diprion spp., Diprionidae, *Gilpinia polytoma*, Hoplocampa spp., Lasius spp., *Monomorium pharaonis*, Neodiprion spp., Solenopsis spp. and Vespa spp.;

from the order of the Diptera, for example Aeries spp., *Antherigona soccata, Bibio hortulanus, Calliphora erythrocephala*, Ceratitis spp., Chrysomyia spp., Culex spp., Cuterebra spp., Dacus spp., *Drosophila melanogaster*, Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami*, Phorbia spp., *Rhagoletis pomonella*, Sciara spp., Stomoxys spp., Tabanus spp., Tannia spp. and Tipula spp.;

from the order of the Siphonaptera, for example Ceratophyllus spp. and *Xenopsylla cheopis* and from the order of the Thysanura, for example *Lepisma saccharina*.

The good pesticidal activity of the compounds according to the invention corresponds to a mortality of at least 50 to 60% of the mentioned pests.

The activity of the compounds according to the invention and of the compositions that comprise those compounds can be substantially broadened and adapted to prevailing circumstances by the addition of other insecticides. Suitable additives are, for example, representatives of the following classes of active substance: organophosphorus compounds, nitrophenols and derivatives thereof, formamidines, ureas, carbamates, pyrethroids, chlorinated hydrocarbons and Bacillus thuringiensis preparations.

The compounds according to the invention are used in unmodified form or, preferably, together with the adjuvants conventionally employed in formulation technology, and can therefore be processed in known manner e.g. into emulsifiable concentrates, directly sprayable or dilutable solutions, dilute emulsions, wettable powders, soluble powders, dusts and granules, and also encapsulations in polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures comprising the compound (active ingredient) according to the invention, or a combination of that compound with other insecticides, and, where appropriate, solid or liquid adjuvants, are prepared in known manner, e.g. by homogeneously mixing and/or grinding the active ingredient with the adjuvants, such as extenders, e.g. solvents or solid carriers, or such as surface-active compounds (surfactants).

Suitable solvents are: aromatic hydrocarbons, preferably the fractions containing 8 to 12 carbon atoms of alkylbenzenes, such as xylene mixtures or alkylated naphthalenes, aliphatic or cycloaliphatic hydrocarbons, such as cyclohexane, paraffins or tetrahydronaphthalene, alcohols, such as ethanol, propanol or butanol, glycols and their ethers and esters, such as propylene glycol, dipropylene glycol ether, ethylene glycol, ethylene glycol monomethyl or monoethyl ether, ketones, such as cyclohexanone, isophorone or diacetone alcohol, strongly polar solvents such as N-methyl-2-pyrrolidone, dimethyl sulfoxide or N,N-dimethylformamide, water and vegetable oils or epoxidised vegetable oils, such as rape, castor, coconut or soybean oil or epoxidised rape, castor, coconut or soybean oil; and, where appropriate, also silicone oils.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are calcite or sand. In addition, a great number of granulated materials of inorganic or organic nature can be used, especially dolomite or pulverised plant residues.

Depending on the nature of the compound according to the invention to be formulated or the combination of that compound with other insecticides, suitable surface-active compounds are non-ionic, cationic and/or anionic surfactants having good emulsifying, dispersing and wetting properties. The term "surfactants" will also be understood as comprising mixtures of surfactants.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic suffactants am the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic suffactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyl-trimethylammonium chloride or benzyldi(2-chloroethyl)ethylammonium bromide.

Both so-called water-soluble soaps and water-soluble synthetic surface-active compounds are suitable anionic surfactants. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil; fatty acid methyltaurin salts may also be mentioned as surfactants. More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and generally contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing approximately 8 to 22 carbon atoms. Examples of alkylarylsulfonates are the sodium, calcium or triethanolammonium salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 tool of ethylene oxide, or phospholipids.

The surfactants indicated above are to be regarded only as examples; the relevant literature describes many other surfactants that are customarily employed in formulation technology and are suitable according to the invention.

The pesticidal compositions generally comprise 0.1 to 99%, especially 0.1 to 95%, of a compound according to the invention or a combination of that compound with other insecticides, and 1 to 99.9%, especially 5 to 99.9%, of a solid or liquid adjuvant, it being possible for 0 to 25%, especially 0.1 to 20%, of the composition to consist of a surfactant (% denotes percentage by weight in each case). Whereas commercial products will preferably be formulated as concentrates, the end user will normally employ dilute formulations, which comprise substantially lower concentrations of active ingredient. Typical application concentrations are 0.1 to 1000 ppm, preferably 0.1 to 500 ppm of active ingredient. The rates of application per hectare are generally 1 to 1000 g of active ingredient per hectare, preferably 25 to 500 g/ha.

Preferred formulations are composed especially of the following constituents (throughout, percentages are by weight):

Emulsifiable concentrates:
active ingredient: 1 to 90%, preferably 5 to 20%
surfactant: 1 to 30%, preferably 10 to 20%
liquid carrier: 5 to 94%, preferably 70 to 85%
Dusts:
active ingredient: 0.1 to 10%, preferably 0.1 to 1%
solid carrier: 99.9 to 90%, preferably 99.9 to 99%
Suspension concentrates:
active ingredient: 5 to 75%, preferably 10 to 50%
water: 94 to 24%, preferably 88 to 30%
surfactant: 1 to 40%, preferably 2 to 30%
Wettable powders:
active ingredient: 0.5 to 90%, preferably 1 to 80%
surfactant: 0.5 to 20%, preferably 1 to 15%
solid carrier: 5 to 95%, preferably 15 to 90%
Granules:
active ingredient: 0.5 to 30%, preferably 3 to 15%
solid carrier: 99.5 to 70%, preferably 97 to 85%

The compositions may also comprise further adjuvants such as stabilisers, for example vegetable oils or epoxidised vegetable oils (for example epoxidised coconut oil, rape oil or soybean oil), antifoams, for example silicone oil, preservatives, viscosity regulators, binders and/or tackifiers, as well as fertilisers or other active ingredients for obtaining special effects.

The following Examples serve to illustrate the invention. They do not limit the invention. Temperatures are given in degrees Celsius.

PREPARATION EXAMPLES

Example P1:

1-(4-Chlorophenyl)-5-ethanesulfonyl-2,3,5-triaza-1-(4-trifluoromethanesulfonyloxyphenyl)-penta-1,4-diene

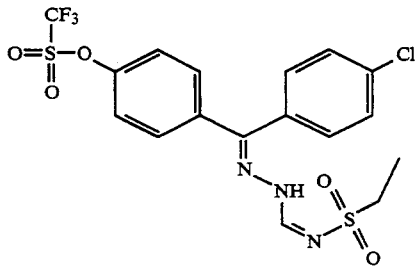

and 1-(4-chlorophenyl)-5-ethanesulfonyl-2,3,5-triaza-1-(4-trifluoromethanesulfonyloxyphenyl)-penta-1,3-diene

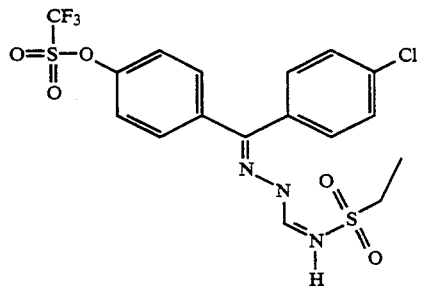

15.7 g of 1-aza-1-ethanesulfonyl-3-oxa-pent-1-ene and 28 ml of triethylamine are added to a solution of 15.2 g of 4-chloro-4'-trifluoromethanesulfonyloxy-benzophenonehydrazone in 150 ml of 1,4-dioxane. The mixture is stirred for 17 hours under reflux, cooled to room temperature and concentrated by evaporation in vacuo using a rotary evaporator. The residue is chromatographed on silica gel using dichloromethane as eluant to give the title compound in the form of a mixture of isomers that melts at from 121° to 129° C. (compound no. 1.2).

Example P2:

1-(4-Chlorophenyl)-2,3-diaza-4-methyl-6-oxo-1-(4-trifluoromethanesulfonyloxyphenyl)-hepta-1,4-diene

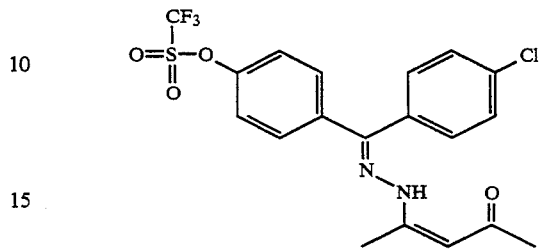

and 1-(4-chlorophenyl)-2,3-diaza-4-methyl-6-oxo-1-(4-trifluoromethanesulfonyloxyphenyl)-hepta-1,3-diene

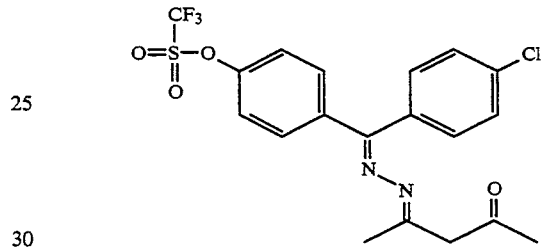

1.2 g of pentane-2,4-dione and 0.5 ml of glacial acetic acid are added to a solution of 3.8 g of 4-chloro-4'-trifluoromethanesulfonyloxy-benzophenonehydrazone in 50 ml of toluene. The reaction mixture is stirred for 12 hours under reflux, cooled to room temperature and concentrated by evaporation in vacuo using a rotary evaporator. The residue is chromatographed on silica gel at a pressure of 35 bar using ethyl acetate/hexane (1:20) as eluant to give the title compound in the form of an oily mixture of isomers (compound no. 3.5).

Example P3:

In a manner analogous to that described in Examples P1 and P2, it is also possible to prepare the other compounds of formula I listed in Tables 1 to 5, or, where appropriate, the tautomers thereof. If mixtures of isomers were separated into two components, the individual components are marked "A" or "B". In the column "m.p." of the Tables, the temperatures given indicate the melting point of the compound concerned.

TABLE 1

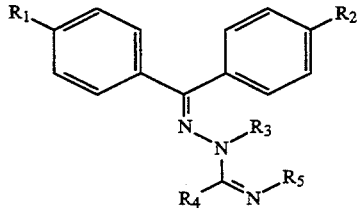

| Comp. No. | $R_1$ | $R_2$ | $R_3$ | $R_4$ | $R_5$ | m.p. °C. |
|---|---|---|---|---|---|---|
| 1.1 | —OSO$_2$CF$_3$ | Cl | H | H | —SO$_2$CH$_3$ | 121–129 |
| 1.2 | —OSO$_2$CF$_3$ | Cl | H | H | —SO$_2$CH$_2$CH$_3$ | 75–80 |
| 1.3 | —OSO$_2$CF$_3$ | Cl | H | H | —SO$_2$n-C$_4$H$_9$ | amorphous |
| 1.4 | —OSO$_2$CF$_3$ | Cl | H | H | —SO$_2$C$_6$H$_5$ | 176–178 |
| 1.5 | —OSO$_2$CF$_3$ | Cl | H | H | —SO$_2$C$_6$H$_4$-4-CH$_3$ | 155–160 |
| 1.6 | —OSO$_2$CF$_3$ | Cl | H | H | —SO$_2$C$_6$H$_4$-4-Cl | amorphous |

TABLE 1-continued

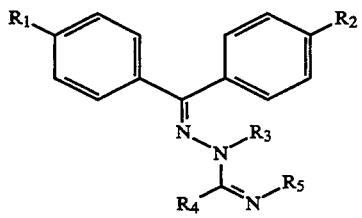

| Comp. No. | R₁ | R₂ | R₃ | R₄ | R₅ | m.p. °C. |
|---|---|---|---|---|---|---|
| 1.7 | —OSO₂CF₃ | Cl | H | H | —SO₂C₆H₄-4-I | 98 |
| 1.8 | —OSO₂CF₃ | Cl | H | H | —SO₂C₆H₄-4-OCH₃ | amorphous |
| 1.9 | —OSO₂CH₃ | Cl | H | H | —SO₂CH₃ | amorphous |
| 1.10 | —OSO₂CH₃ | Cl | H | H | —SO₂CH₂CH₃ | 85–105 |
| 1.11 | —OSO₂CH₃ | Cl | H | H | —SO₂C₆H₄-4-CH₃ | 47–51 |
| 1.12 | —H | H | H | H | —SO₂CH₂CH₃ | 145 |
| 1.13A | —OH | Cl | H | H | —SO₂CH₂CH₃ | 86–108 |
| 1.13B | —OH | Cl | H | H | —SO₂CH₂CH₃ | 162–170 |
| 1.14A | —OH | Cl | H | H | —SO₂CH₃ | 177–185 |
| 1.14B | —OH | Cl | H | H | —SO₂CH₃ | 168–173 |
| 1.15 | —OSO₂CH₃ | Cl | CH₃ | H | —SO₂CH₂CH₃ | foam |
| 1.16 | —OSO₂CF₃ | Cl | CH₃ | H | —SO₂CH₂CH₃ | resin |
| 1.17 | —OSO₂CF₃ | Cl | H | CH₃ | —SO₂CH₃ | resin |
| 1.18 | —OSO₂CF₃ | Cl | H | CH₃ | —SO₂CH₂CH₃ | resin |
| 1.19 | —OSO₂CF₃ | Cl | H | H | —SO₂CH₂Cl | amorphous |
| 1.20 | —OSO₂CF₃ | Cl | H | H | —SO₂CH₂Br | |
| 1.21 | —OSO₂CF₃ | F | H | H | —SO₂CH₃ | 168–171 |
| 1.22 | —OSO₂CF₃ | F | H | H | —SO₂CH₂CH₃ | 65 |
| 1.23 | —OSO₂CF₃ | F | H | H | —SO₂CH₂CH₂CH₃ | |
| 1.24 | —OSO₂CF₃ | F | H | H | —SO₂CH(CH₃)₂ | |
| 1.25 | —OSO₂CF₃ | Cl | H | H | —SO₂CH₂CH₂CH₃ | resin |
| 1.26 | —OSO₂CF₃ | Cl | H | H | —SO₂CH(CH₃)₂ | resin |
| 1.27 | —OSO₂CF₃ | Cl | H | H | —SO₂CH₂CH(CH₃)₂ | |
| 1.28 | —OSO₂CF₃ | Cl | H | H | —SO₂C(CH₃)₃ | |
| 1.29 | —OSO₂CF₃ | Cl | H | H | —SO₂CH₂C(CH₃)₃ | |
| 1.30 | —OSO₂CF₃ | Cl | H | H | —SO₂-cyclo-C₃H₅ | |
| 1.31 | —OSO₂CF₂CF₂Cl | Cl | H | H | —SO₂CH₃ | |
| 1.32 | —OSO₂CF₂CF₂Cl | Cl | H | H | —SO₂CH₂CH₃ | |
| 1.33 | —OSO₂CF₂CF₃ | Cl | H | H | —SO₂CH₃ | |
| 1.34 | —OSO₂CF₂CF₃ | Cl | H | H | —SO₂CH₂CH₃ | |
| 1.35 | —OSO₂CF₃ | Cl | H | H | —CN | |
| 1.36 | —OSO₂CF₃ | Cl | H | H | —CO₂CH₃ | |
| 1.37 | —OSO₂CF₃ | Cl | H | H | —CO₂CH₂CH₃ | |
| 1.38 | —OSO₂CH₂Cl | Cl | H | H | —SO₂CH₃ | 55–66 |
| 1.39 | —OSO₂CH₂Cl | Cl | H | H | —SO₂CH₂CH₃ | foam |
| 1.40 | —OSO₂CF₃ | Cl | H | H | —SO₂CH₂C₆H₅ | amorphous |
| 1.41 | —OSO₂CF₃ | Cl | CH₃ | H | —SO₂CH₃ | resin |
| 1.42A | —OSO₂CF₃ | F | H | H | —SO₂C₆H₅ | 65–67 |
| 1.42B | —OSO₂CF₃ | F | H | H | —SO₂C₆H₅ | 75–78 |
| 1.43 | —OSO₂CF₃ | F | H | H | —SO₂CH₂C₆H₅ | 74–81 |
| 1.44 | —OSO₂CF₃ | F | H | CH₃ | —SO₂C₂H₅ | oil |
| 1.45 | —OSO₂CF₃ | F | CH₃ | H | —SO₂C₂H₅ | oil |
| 1.46 | —NO₂ | Cl | H | H | —SO₂C₂H₅ | 88–95 |
| 1.47 | —N(C₂H₅)SO₂CF₃ | Cl | H | H | —SO₂C₂H₅ | amorphous |
| 1.48A | —OSO₂CF₃ | Br | H | H | —SO₂CH₂C₆H₅ | wax |
| 1.48B | —OSO₂CF₃ | Br | H | H | —SO₂CH₂C₆H₅ | wax |
| 1.49 | —OSO₂CF₃ | CH₃ | H | H | —SO₂C₂H₅ | 95–97 |
| 1.50 | —OSO₂CF₃ | CH₃ | H | H | —SO₂CH₂C₆H₅ | 122–140 |
| 1.51 | —OSO₂CF₃ | CH₃ | H | H | —SO₂C₆H₅ | 171–175 |
| 1.52 | —OSO₂CF₃ | t-C₄H₉ | H | H | —SO₂CH₂C₆H₅ | 122–132 |
| 1.53 | —OSO₂CF₃ | t-C₄H₉ | H | H | —SO₂C₆H₅ | 153–155 |
| 1.54 | —OSO₂CF₃ | t-C₄H₉ | H | CH₃ | —SO₂C₂H₅ | oil |
| 1.55 | —OSO₂CF₃ | t-C₄H₉ | H | H | —SO₂C₂H₅ | 172–176 |
| 1.56 | —OC₆H₅ | Cl | H | H | —SO₂CH₂C₆H | wax |
| 1.57 | —OC₆H₅ | Cl | H | H | —SO₂C₂H₅ | wax |
| 1.58 | —OC₆H₅ | Cl | H | H | —SO₂C₆H₅ | wax |
| 1.59 | —OCF₂CHF₂ | F | H | H | —SO₂N(CH₃)₂ | resin |
| 1.60 | —OCF₂CHF₂ | Cl | H | H | —SO₂C₂H₅ | foam |
| 1.61 | —OSO₂CH₃ | Br | H | H | —SO₂C₂H₅ | foam |
| 1.62 | —OSO₂C₆H₅ | Cl | H | H | —SO₂CH₂C₆H₅ | wax |
| 1.63 | —OSO₂C₆H₅ | Cl | H | H | —SO₂C₆H₅ | 88–100 |
| 1.64 | —OSO₂C₆H₅ | Cl | H | H | —SO₂C₂H₅ | 95–103 |

TABLE 2

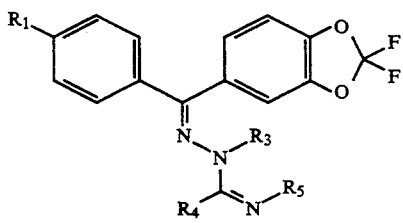

| Comp. No. | R₁ | R₃ | R₄ | R₅ | m.p. °C. |
|---|---|---|---|---|---|
| 2.1 | Cl | H | H | —SO₂CH₃ | 181–183.5 |
| 2.2 | Cl | H | H | —SO₂CH₂CH₃ | 65–70 |
| 2.3 | Cl | H | H | —SO₂CH₂CH₂CH₃ | |
| 2.4 | Cl | H | H | —SO₂(CH₂)₃CH₃ | |
| 2.5 | Cl | H | H | —SO₂CH(CH₃)₂ | |
| 2.6 | Cl | H | H | —SO₂CH₂CH(CH₃)₂ | |

TABLE 4

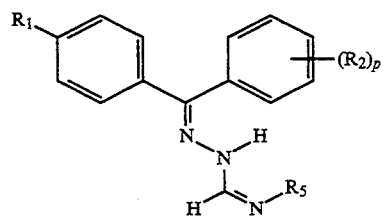

| Comp. No. | R₁ | R₂ | R₅ | m.p. °C. |
|---|---|---|---|---|
| 4.1A | —OSO₂CF₃ | 3-Cl | —SO₂C₂H₅ | oil |
| 4.1B | —OSO₂CF₃ | 3-Cl | —SO₂C₂H₅ | 80–89 |
| 4.2A | —OSO₂CF₃ | 3-Cl | —SO₂CH₂C₆H₅ | wax |
| 4.2B | —OSO₂CF₃ | 3-Cl | —SO₂CH₂C₆H₅ | 100–109 |
| 4.3 | —OSO₂CF₃ | 3-Cl | —SO₂C₆H₅ | 104–116 |
| 4.4 | —OSO₂CF₃ | 3,4-Cl₂ | —SO₂C₆H₅ | wax |
| 4.5 | —OSO₂CF₃ | 3,4-Cl₂ | —SO₂C₂H₅ | oil |
| 4.6 | —OSO₂CF₃ | 2,4-Cl₂ | —SO₂C₂H₅ | wax |
| 4.12 | —OSO₂CF₃ | 2,4-Cl₂ | —SO₂C₆H₅ | wax |
| 4.13 | —OSO₂CF₃ | 2-Cl | —SO₂CH₂C₆H₅ | wax |
| 4.14 | —OSO₂CF₃ | 2-Cl | —SO₂C₆H₅ | wax |
| 4.15 | —OSO₂CF₃ | 2-Cl | —SO₂C₂H₅ | wax |

TABLE 3

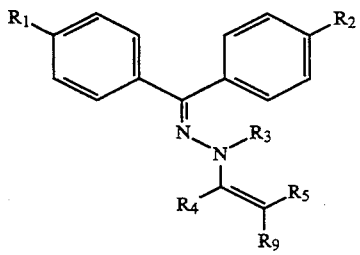

| Comp. No. | R₁ | R₂ | R₃ | R₄ | R₅ | R₉ | m.p. °C. |
|---|---|---|---|---|---|---|---|
| 3.1A | —OSO₂CH₃ | Cl | H | CH₃ | —C(=O)CH₃ | H | 124–125 |
| 3.1B | —OSO₂CH₃ | Cl | H | CH₃ | —C(=O)CH₃ | H | 143–144 |
| 3.2 | —OSO₂CH₃ | Cl | H | CF₃ | —C(=O)CH₃ | H | foam |
| 3.3 | —OSO₂CH₃ | Cl | H | CF₃ | —C(=O)CF₃ | H | 126–127.5 |
| 3.4 | —OSO₂CH₃ | Cl | H | C₆H₅ | —C(=O)CH₃ | H | 118–122 |
| 3.5 | —OSO₂CF₃ | Cl | H | CH₃ | —C(=O)CH₃ | H | oil |
| 3.5A | —OSO₂CF₃ | Cl | H | CH₃ | —C(=O)CH₃ | H | 118–120 |
| 3.5B | —OSO₂CF₃ | Cl | H | CH₃ | —C(=O)CH₃ | H | oil |
| 3.6 | —OSO₂CF₃ | Cl | H | CF₃ | —C(=O)CH₃ | H | resin |
| 3.7 | —OSO₂CF₃ | Cl | H | CF₃ | —C(=O)CF₃ | H | resin |
| 3.8 | —OSO₂CF₃ | Cl | H | C₆H₅ | —C(=O)CH₃ | H | 97–102 |
| 3.9 | —OH | Cl | H | CH₃ | —C(=O)CH₃ | H | 194–197 |
| 3.10 | —OSO₂CF₃ | Cl | H | H | —CN | —CN | 182–186 |
| 3.11 | —OSO₂CF₃ | Cl | H | H | —CN | —C(=O)OC₂H₅ | 152–154° |
| 3.12 | —OSO₂CF₃ | Cl | H | H | —C(=O)OC₂H₅ | —C(=O)OC₂H₅ | 85–87° |
| 3.13A | —OSO₂CF₃ | Cl | H | CH₃ | —C(=O)OCH₃ | H | 130–134° |
| 3.13B | —OSO₂CF₃ | Cl | H | CH₃ | —C(=O)OCH₃ | H | 90–92° |
| 3.14 | —OSO₂CF₃ | Cl | H | CH₃ | —C(=O)OC₂H₅ | H | 86–90° |
| 3.15 | —OSO₂CF₃ | Cl | H | CH₃ | —C(=O)O-t-Bu | H | 109–117° |
| 3.16 | —OSO₂CH₃ | Cl | H | CH₃ | —C(=O)O-t-Bu | H | 116–120° |
| 3.17A | —OSO₂CF₃ | CH₃ | H | CH₃ | —C(=O)CH₃ | H | 114–117 |
| 3.17B | —OSO₂CF₃ | CH₃ | H | CH₃ | —C(=O)CH₃ | H | wax |
| 3.18 | —OSO₂CF₃ | t-C₄H₉ | H | CH₃ | —C(=O)CH₃ | H | oil |
| 3.19A | —OSO₂CF₃ | F | H | CH₃ | —C(=O)CH₃ | H | 95–97 |
| 3.19B | —OSO₂CF₃ | F | H | CH₃ | —C(=O)CH₃ | H | 96–97 |
| 3.20A | —OSO₂CF₃ | F | H | C₂H₅ | —C(=O)C₂H₅ | H | 126–127 |
| 3.20B | —OSO₂CF₃ | F | H | C₂H₅ | —C(=O)C₂H₅ | H | resin |
| 3.21A | —OSO₂CF₃ | F | H | i-C₃H₇ | —C(=O)C₃H₉-i | H | 123–124 |
| 3.21B | —OSO₂CF₃ | F | H | i-C₃H₇ | —C(=O)C₃H₉-i | H | 75–77 |
| 3.22A | —OSO₂CF₃ | Br | H | CH₃ | —C(=O)CH₃ | H | 120–122 |
| 3.22B | —OSO₂CF₃ | Br | H | CH₃ | —C(=O)CH₃ | H | 104–107 |
| 3.23A | —OSO₂CF₃ | CH₃ | H | CH₃ | —C(=O)CH₃ | H | 114–117 |
| 3.23B | —OSO₂CF₃ | CH₃ | H | CH₃ | —C(=O)CH₃ | H | wax |
| 3.24 | —OSO₂CF₃ | t-C₄H₉ | H | CH₃ | —C(=O)CH₃ | H | oil |

TABLE 5

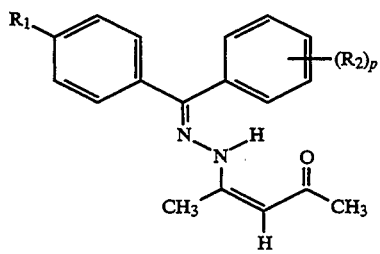

| Comp. No. | $R_1$ | $R_2$ | m.p. °C. |
|---|---|---|---|
| 5.1A | —OSO$_2$CF$_3$ | 3-Cl | 91–93 |
| 5.1B | —OSO$_2$CF$_3$ | 3-Cl | 94–97 |
| 5.2 | —OSO$_2$CF$_3$ | 3,4-Cl$_2$ | 92–94 |

Formulation Examples (throughout, percentages are by weight)

Example F1: Emulsifiable concentrates

|  | a) | b) | c) |
|---|---|---|---|
| compound no. 1.2 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

Example F2: Solutions

|  | a) | b) | c) | d) |
|---|---|---|---|---|
| compound no. 1.2 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

Example F3: Granules

|  | a) | b) | c) | d) |
|---|---|---|---|---|
| compound no. 1.2 | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution is sprayed onto the carrier, and the solvent is subsequently evaporated off in vacuo.

Example F4: Dusts

|  | a) | b) |
|---|---|---|
| compound no. 1.2 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Example F5: Wettable powders

|  | a) | b) | c) |
|---|---|---|---|
| compound no. 1.2 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is thoroughly ground in a suitable mill, affording wettable powders which can be diluted with water to give suspensions of the desired concentration.

Example F6: Emulsifiable concentrate

| compound no. 1.2 | 10% |
|---|---|
| octylphenol polyethylene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

Example F7: Dusts

|  | a) | b) |
|---|---|---|
| compound no. 1.2 | 5% | 8% |
| talcum | 95% | — |
| kaolin | — | 92% |

Ready-for-use dusts are obtained by mixing the active ingredient with the carrier and grinding the mixture in a suitable mill.

Example F8: Extruder granules

| compound no. 1.2 | 10% |
|---|---|
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded, granulated and then dried in a stream of air.

Example F9: Coated granules

| compound no. 1.2 | 3% |
|---|---|
| polyethylene glycol (mol. wt. 200) | 3% |

| | |
|---|---|
| kaolin | 94% |

The finely ground active ingredient is uniformly applied, in a mixer, to the kaolin moistened with polyethylene glycol. Non-dusty coated granules are obtained in this manner.

Example F10: Suspension concentrate

| | |
|---|---|
| compound no. 1.2 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Biological Examples

Example B1: Action against *Spodoptera littoralis*

Young soybean plants are sprayed with an aqueous emulsion spray mixture containing the test compound in a concentration of 400 ppm. After the spray coating has dried, each of the plants is populated with 10 caterpillars of *Spodoptera littoralis* in the third stage and placed in a plastics container. Evaluation is made 3 days later. The percentage reduction in the population and the percentage reduction in feeding damage (% action) are determined by comparing the treated plants and the untreated planks in respect of the number of dead caterpillars and feeding damage.

Compounds of Tables 1 to 5 exhibit good activity in this test. In particular, compounds nos. 1.1, 1.2, 1.3, 1.5, 1.6, 1.7, 1.8, 1.9, 1.11, 1.16, 1.17, 1.21, 1.22, 1.25, 1.41, 1.42A, 1.42B, 3.5, 3.19A, 3.19B, 3.20A and 3.20B are more than 80 % effective.

Example B2: Action against *Diabrotica balteata*

Maize seedlings are sprayed with an aqueous emulsion spray mixture containing the test compound in a concentration of 400 ppm. After the spray coating has dried, each of the seedlings is populated with 10 larvae of *Diabrotica balteats* in the second stage and placed in a plastics container. Evaluation is made 6 days later. The percentage reduction in the population (% action) is determined by comparing the treated plants and the untreated plants in respect of the number of dead larvae.

Compounds of Tables 1 to 5 exhibit good activity in this test. In particular, compounds nos. 1.1, 1.2, 1.3, 1.6, 1.7, 1.11, 1.16, 1.17, 1.21, 1.22, 1.25, 1.41, 2.1, 2.2, 3.13.19A, 3.19B, 3.20A, 3.20B, 3.22A and 3.22B are more than 80% effective.

Example B3: Ovicidal action against *Heliothis virescens*

Eggs of *Heliothis virescens* deposited on filter paper are immersed for a short time in an acetonic-aqueous test solution containing the test compound in a concentration of 400 ppm. After the test solution has dried, the eggs are incubated in petri dishes. 6 days later, the percentage hatching of the eggs is evaluated in comparison with untreated control batches (% reduction in hatching).

Compounds of Tables 1 to 5 exhibit good activity in this test. In particular, compounds nos. 1.1, 1.2, 1.3, 1.4, 1.5, 1.6, 1.7, 1.8, 1.9, 1.10, 1.12, 1.16, 1.17, 1.21, 1.22, 1.25, 1.41, 1.42A, 1.42B, 3.1, 3.5, 3.6, 3.19A, 3.19B, 3.20B, 3.22A, 3.22B, 4.4 and 4.5 are more 80% effective.

Example B4: Action against *Heliothis virescens*

Young soybean plants are sprayed with an aqueous emulsion spray mixture containing the test compound in a concentration of 400 ppm. After the spray coating has dried, each of the plants is populated with 10 caterpillars of *Heliothis virescens* in the first stage and placed in a plastics container. Evaluation is made 6 days later. The percentage reduction in the population and the percentage reduction in feeding damage (% action) are determined by comparing the treated plants and the untreated plants in respect of the number of dead caterpillars and feeding damage.

Compounds of Tables 1 to 5 exhibit good activity in this test. In particular, compounds nos. 1.1, 1.2, 1.3, 1.4, 1.5, 1.6, 1.7, 1.8, 1.9, 1.10, 1.11, 1.16, 1.17, 1.21, 1.22, 1.25, 1.42A, 1.42B, 3.1, 3.19A and 3.19B are more than 80% effective.

Example B5: Action against *Crocidolomia binotalis*

Young cabbage plants are sprayed with an aqueous emulsion spray mixture containing the test compound in a concentration of 400 ppm. After the spray coating has dried, each of the cabbage plants is populated with 10 caterpillars of *Crocidolomia binotalis* in the third stage and placed in a plastics container. Evaluation is made 3 days later. The percentage reduction in the population and the percentage reduction in feeding damage (% action) are determined by comparing the treated plants and the untreated plants in respect of the number of dead caterpillars and feeding damage.

Compounds of Tables 1 to 5 exhibit good activity in this test. In particular, compounds nos. 1.1, 1.2, 1.3, 1.5, 1.6, 1.7, 1.8 and 3.2 are more than 80% effective.

Example B6: Action against *Plutella xylostella*

Young cabbage plants are sprayed with an aqueous emulsion spray mixture containing the test compound in a concentration of 400 ppm. After the spray coating has dried, each of the plants is populated with 10 caterpillars of *Plutella xylostella* in the third stage and placed in a plastics container. Evaluation is made 3 days later. The percentage reduction in the population and the percentage reduction in feeding damage (% action) are determined by comparing the treated plants and the untreated plants in respect of the number of dead caterpillars and feeding damage.

Compounds of Tables 1 to 5 exhibit good activity in this test. In particular, compounds nos. 1.17, 1.19, 1.20, 1.26, 1.27, 3.5, 3.6, 3.7 and 3.10 are more than 80% effective.

Example B7: Action against *Lucilia cuprina* blowflies

Freshly deposited eggs of the blowfly species *Lucilia cuprina* are put in small portions (30–50 eggs) into each of a number of test tubes in which 4 ml of nutrient medium have been mixed with 1 ml of test solution containing the test compound in a concentration of 16 ppm. After inoculation of the culture medium, the test tubes are sealed with cotton wool plugs and are then incubated in an incubator at 30° C. for 4 days. In the untreated medium, larvae about 1 cm in length (stage 3) have developed by the end of this 4-day period. When a substance is active, by the end of this period the larvae are either dead or their development is distinctly retarded. Evaluation is made after 96 hours.

The compounds of Tables 1 to 5 exhibit good activity against *Lucilia cuprina* in this test. In particular, compounds nos. 1.1, 1.2, 1.4, 1.5, 1.7, 1.8, 1.19, 1.40 and 1.41 are more than 80% effective.

Example B8: Stomach toxicant action against *Ctenocephalides felis* (systemic)

20 adult fleas of the species *Ctenocephalides felis* are placed in a flat round cage sealed on both sides with gauze. A container closed at the bottom by a parafilm membrane is placed on this cage. The container holds blood that contains the test compound in a concentration of 50 ppm and is heated constantly at 37° C. The fleas take up the blood through the membrane. Evaluation is made 24 and 48 hours after the beginning of the test. The percentage reduction in the population (% action) is determined by comparing the number of dead fleas with treated blood and the number of dead fleas with untreated blood. 24 hours after treatment, the blood is replaced by fresh blood which has also been treated.

The compounds of Tables 1 to 5 exhibit good activity against *Ctenocephalides felis* in this test. In particular, compounds nos. 1.1, 1.2, 1.4, 1.5, 1.7, 1.8, 1.19 and 1.41 are more than 80% effective.

What is claimed is:
1. A compound of the formula

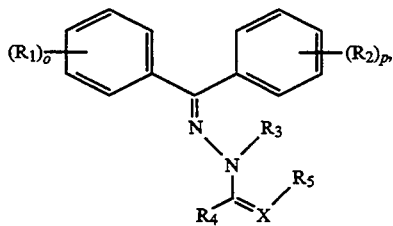

wherein
each of o and p, independently of the other, is 0, 1, 2, 3, 4 or 5, the radicals $R_1$ being the same or different when o is greater than 1 and the radicals $R_2$ being the same or different when p is greater than 1;
each of $R_1$ and $R_2$, independently of the other, is selected from the group consisting of $C_1-C_4$alkyl, halo-$C_1-C_4$alkyl, halogen, —$NO_2$, —OH, $C_1-C_4$alkoxy, halo-$C_1-C_4$alkoxy, $C_1-C_4$alkylthio, halo-$C_1-C_4$alkylthio, —O—S(=O)—$R_6$, —O—S(=O)$_2$—$R_6$, phenoxy or —N($R_{11}$)SO$_2R_{12}$ and two substituents $R_1$ bonded to vicinal carbon atoms of the phenyl ring and/or two substituents $R_2$ bonded to vicinal carbon atoms of the phenyl ring are, independently of one another, together —Y—Z—Y—;
$R_3$ is hydrogen, $C_1-C_4$alkyl or halo-$C_1-C_4$alkyl;
$R_4$ is hydrogen, $C_1-C_4$alkyl, halo-$C_1-C_4$alkyl, unsubstituted phenyl or naphthyl or mono- or di-substituted phenyl or naphthyl, the substituents being selected from the group consisting of halogen, $C_1-C_4$alkyl, halo-$C_1-C_4$alkyl, $C_1-C_4$alkyloxy, halo-$C_1-C_4$alkoxy, $C_1-C_4$alkylthio, halo-$C_1-C_4$alkylthio, —$NO_2$ and —CN;

$R_5$ is —S—$R_7$, —S(=O)—$R_7$, —S(=O)$_2$—$R_7$, —$NO_2$, —CN, —C(=O)—$R_8$ or —C(=O)—$OR_8$;
$R_6$ is $C_1-C_8$alkyl, or halo-$C_1-C_8$alkyl or phenyl;
$R_7$ is $C_1-C_8$alkyl, $C_3-C_6$cycloalkyl, halo-$C_1-C_8$alkyl, unsubstituted or mono- or di-substituted phenyl, the substituents being selected from the group consisting of halogen, $C_1-C_4$alkyl, halo-$C_1-C_4$alkyl, $C_1-C_4$alkoxy, halo-$C_1-C_4$alkoxy, $C_1-C_4$alkylthio, halo-$C_1-C_4$alkylthio, —$NO_2$ and —CN; benzyl or unsubstituted or mono- or di-substituted amino, the substituents being selected from the group consisting of $C_1-C_4$alkyl, halo-$C_1-C_4$alkyl and phenyl;
$R_8$ is $C_1-C_8$alkyl, halo-$C_1-C_8$alkyl or unsubstituted or mono- or di-substituted phenyl, the substituents being selected from the group consisting of halogen, $C_1-C_4$alkyl, halo-$C_1-C_4$alkyl, $C_1-C_4$alkoxy, halo-$C_1-C_4$alkoxy, $C_1-C_4$alkylthio, halo-$C_1-C_4$alkylthio, —$NO_2$ and —CN;
X is N;
each Y, independently of the other, is O or S;
Z is methylene, eth-1,2-ylene, halomethylene or haloeth-1,2-ylene;
$R_{11}$ is hydrogen, $C_1-C_4$alkyl or halo-$C_1-C_4$alkyl; and
$R_{12}$ is $C_1-C_4$alkyl, halo-$C_1-C_4$alkyl, unsubstituted or mono- or di-substituted phenyl, the substituents being selected from the group consisting of halogen, $C_1-C_4$alkyl, halo-$C_1-C_4$alkyl, $C_1-C_4$alkoxy, halo-$C_1-C_4$alkoxy, $C_1-C_4$alkylthio, halo-$C_1-C_4$alkylthio, —$NO_2$ and —CN;
or, where appropriate, a tautomer thereof, or a salt thereof or a salt of a tautomer;
with the proviso (A) that, in compounds of formula I in free form wherein each of o and p is 0, $R_4$ is hydrogen and X is N, $R_3$ is other than hydrogen when $R_5$ is methanesulfonyl, unsubstituted phenylsulfonyl or 4-methylphenylsulfonyl.

2. A compound according to claim 1 of formula I in free form.

3. A compound according to claim 1 of formula I wherein o is 1 or 2, the radicals $R_1$ being the same or different when o is 2,
$R_1$ is halogen, —$NO_2$, —OH, —O—S(=O)$_2$—$C_1-C_4$alkyl, —O—S(=O)$_2$-halo-$C_1-C_4$alkyl, phenoxy, —$NO_2$ or —N($R_{11}$)SO$_2R_{12}$ or two substituents $R_1$ bonded to vicinal carbon atoms of the phenyl ring are together —O-methylene-O— or —O-halomethylene-O—, $R_{11}$ is hydrogen or $C_1-C_4$alkyl, and $R_{12}$ is halo-$C_1-C_4$alkyl, or, where appropriate, a tautomer thereof.

4. A compound according to claim 3 of formula I wherein $R_1$ is halogen, —OH, —O—S(=O)$_2$-$C_1-C_4$alkyl, —O—S(=O)$_2$-halo-$C_1-C_4$alkyl, phenoxy or —N($R_{11}$)SO$_2$-halo-$C_1-C_2$alkyl or two substituents $R_1$ bonded to vicinal carbon atoms of the phenyl ring are together —O-methylene-O— or —O-halomethylene-O— and $R_{11}$ is hydrogen or $C_1-C_2$alkyl, or, where appropriate, a tautomer thereof.

5. A compound according to claim 4 of formula I wherein p is 0, 1 or 2, the radicals $R_2$ being the same or different when p is 2, and
$R_2$ is halogen, —OH, —O—S(=O)$_2$-$C_1-C_4$alkyl or —O—S(=O)$_2$-halo-$C_1-C_4$alkyl or two substituents $R_2$ bonded to vicinal carbon atoms of the phenyl ring are together —O-methylene-O— or —O-halomethylene-O—, or, where appropriate, a tautomer thereof.

6. A compound according to claim 5 of formula I wherein p is 0, 1 or 2, the radicals $R_2$ being the same when p is 2, and $R_2$ is halogen, —OH, —O—S(=O)$_2$-C$_1$-C$_2$alkyl or —O—S(=O)$_2$-halo-C$_1$-C$_2$alkyl or two substituents $R_2$ bonded to vicinal carbon atoms of the phenyl ring are together —O-halomethylene-O—, or, where appropriate, a tautomer thereof.

7. A compound according to claim 1 of formula I wherein
$R_3$ is hydrogen or C$_1$-C$_4$alkyl, or, where appropriate, a tautomer thereof.

8. A compound according to claim 1 of formula I wherein
$R_4$ is hydrogen, C$_1$-C$_4$alkyl, halo-C$_1$-C$_4$alkyl or phenyl, or, where appropriate, a tautomer thereof.

9. A compound according to claim 1 of formula I wherein
$R_5$ is —S(=O)$_2$—$R_7$, —CN, —C(=O)—$R_8$ or —C(=O)—OR$_8$,
$R_7$ is C$_1$-C$_6$alkyl, C$_3$-C$_6$cycloalkyl, halo-C$_1$-C$_4$alkyl, benzyl, C$_1$-C$_4$dialkylamino, or phenyl that is unsubstituted or mono-substituted by halogen, C$_1$-C$_4$alkyl or by C$_1$-C$_4$alkoxy,
$R_8$ is C$_1$-C$_4$alkyl, halo-C$_1$-C$_4$alkyl or phenyl, and X is N,
or, where appropriate, a tautomer thereof.

10. A compound according to claim 9 of formula I wherein
$R_5$ is —S(=O)$_2$—$R_7$, —CN, —C(=O)—$R_8$ or —C(=O)—OR$_8$,
$R_7$ is C$_1$-C$_4$alkyl, halo-C$_1$-C$_2$alkyl, benzyl or dimethylamino, or phenyl that is unsubstituted or mono-substituted by halogen, C$_1$-C$_2$alkyl or by C$_1$-C$_2$alkoxy,
$R_8$ is C$_1$-C$_4$alkyl or halo-C$_1$-C$_2$alkyl, and X is N,
or, where appropriate, a tautomer thereof.

11. A compound according to claim 1 of formula I wherein
o is 1 or 2,
p is 0, 1 or 2, the radicals $R_1$ being the same or different when o is 2 and the radicals $R_2$ being the same or different when p is 2;
each of $R_1$ and $R_2$, independently of the other, is halogen, —NO$_2$, —OH, phenoxy, —N(R$_{11}$)SO$_2$CF$_3$ or —O—S(=O)$_2$—R$_6$ or two substituents $R_1$ bonded to vicinal carbon atoms of the phenyl ring or two substituents $R_2$ bonded to vicinal carbon atoms of the phenyl ring are together —O—Z—O—;
$R_3$ is hydrogen or C$_1$-C$_4$alkyl;
$R_4$ is hydrogen, C$_1$-C$_4$alkyl, halo-C$_1$-C$_4$alkyl or unsubstituted phenyl;
$R_5$ is —S(=O)$_2$—$R_7$, —CN, —C(=O)—$R_8$ or —C(=O)—OR$_8$;
$R_6$ is C$_1$-C$_4$alkyl, halo-C$_1$-C$_4$alkyl or phenyl;
$R_7$ is C$_1$-C$_6$alkyl, C$_3$-C$_6$cycloalkyl, halo-C$_1$-C$_4$alkyl, phenyl that is unsubstituted or mono-substituted by halogen, C$_1$-C$_4$alkyl or by C$_1$-C$_4$alkoxy, or is benzyl or dimethylamino;
$R_8$ is C$_1$-C$_4$alkyl or halo-C$_1$-C$_4$alkyl;
X is N; and
Z is methylene or halomethylene;
or —C(=O)—OR$_{10}$;
and
$R_{11}$ is hydrogen, methyl or ethyl, or, where appropriate, a tautomer thereof.

12. A compound according to claim 11 of formula I wherein
o is 1 or 2,
p is 0, 1 or 2, the radicals $R_1$ being the same different when o is 2 and the radicals $R_2$ being the same or different when p is 2;
each of $R_1$ and $R_2$, independently of the other, is halogen, —OH or —O—S(=O)$_2$—R$_6$ or two substituents $R_1$ bonded to vicinal carbon atoms of the phenyl ring or two substituents $R_2$ bonded to vicinal carbon atoms of the phenyl ring are together —O—Z—O—;
$R_3$ is hydrogen or C$_1$-C$_4$alkyl;
$R_4$ is hydrogen, C$_1$-C$_4$alkyl, halo-C$_1$-C$_4$alkyl or unsubstituted phenyl;
$R_5$ is —S(=O)$_2$—$R_7$, —CN, —C(=O)—$R_8$ or —C(=O)—OR$_8$;
$R_6$ is C$_1$-C$_4$alkyl or halo-C$_4$-C$_4$alkyl;
$R_7$ is C$_1$-C$_6$alkyl, C$_3$-C$_6$cycloalkyl, halo-C$_1$-C$_4$alkyl, or phenyl that is unsubstituted or mono-substituted by halogen, C$_1$-C$_4$alkyl or by C$_1$-C$_4$alkoxy, or is benzyl or dimethylamino;
$R_8$ is C$_1$-C$_4$alkyl or halo-C$_1$-C$_4$alkyl;
X is N; and
Z is methylene or halomethylene;
or, where appropriate, a tautomer thereof.

13. The compound according to claim 1 of formula I, 1-(4-chlorophenyl)-5-ethanesulfonyl-2,3,5-triaza-1-(4-trifluoromethanesulfonyloxyphenyl)-penta-1,4-diene and 1-(4-chlorophenyl)-5-ethanesulfonyl-2,3,5-triaza-1-(4-trifluoromethanesulfonyloxyphenyl)-penta-1,3-diene.

14. A pesticidal composition which comprises, as active ingredient, at least one compound according to claim 1 of formula I or, where appropriate, a tautomer thereof, in each case in free form or in agrochemically acceptable salt form, and at least one adjuvant, the proviso (A) mentioned in claim 1 not being applicable.

15. A composition according to claim 14 for the control of insects.

16. A process for the preparation of a composition according to claim 14 which comprises intimately mixing the active ingredient with the adjuvant(s).

17. A method of controlling pests which comprises applying as active ingredient a compound according to claim 1 of formula I or, where appropriate, a tautomer thereof, in each case in free form or in agrochemically acceptable salt form, the proviso (A) mentioned in claim 1 not being applicable, to the pests or the locus thereof.

18. A method according to claim 17 of controlling insects.

19. A method of controlling pests which comprises applying as active ingredient a composition according to claim 14 to the pests or the locus thereof.

* * * * *